United States Patent [19]

Broger et al.

[11] Patent Number: 5,288,928
[45] Date of Patent: Feb. 22, 1994

[54] ASYMMETRICAL HYDROGENATION

[75] Inventors: Emil A. Broger, Magden; Yvo Crameri, Oberwil; Hans P. Isenring, Sissach; Albert Pfiffner, Bülach, all of Switzerland

[73] Assignee: Ciba-Geigy Corporation, Ardsley, N.Y.

[21] Appl. No.: 916,926

[22] Filed: Jul. 20, 1992

Related U.S. Application Data

[62] Division of Ser. No. 811,381, Dec. 20, 1991, abandoned.

[30] Foreign Application Priority Data

Dec. 21, 1990 [CH] Switzerland ............ 4100/90-9

[51] Int. Cl.$^5$ .................. C07C 29/17; C07C 33/34; C07C 33/46; C07C 27/00
[52] U.S. Cl. .................. 568/807; 568/812; 568/814
[58] Field of Search .......... 568/814, 812, 807

[56] References Cited

U.S. PATENT DOCUMENTS

| | | | |
|---|---|---|---|
| 4,202,894 | 5/1980 | Pfiffner | 424/248 |
| 4,231,938 | 11/1980 | Monaghan et al. | 260/343.5 |
| 4,241,058 | 12/1980 | Pfiffner | 424/248 |
| 4,384,116 | 5/1983 | Pfiffner | 544/178 |
| 4,410,734 | 10/1983 | Martin et al. | 568/715 |
| 4,613,610 | 9/1986 | Wareing | 514/406 |
| 4,681,893 | 7/1987 | Roth | 514/422 |
| 4,879,416 | 11/1989 | Puckette et al. | 568/815 |
| 4,923,884 | 5/1990 | Chandraratna | 514/354 |

FOREIGN PATENT DOCUMENTS

| | | |
|---|---|---|
| 0306929 | 3/1989 | European Pat. Off. |
| 0307342 | 3/1989 | European Pat. Off. |
| 0319847 | 6/1989 | European Pat. Off. |

OTHER PUBLICATIONS

Miyashita et al., J. Am. Chem. Soc., 102, 7932 (1980).
Miyashita et al., Tetrahedron, 40, 1245 (1984).
Tani et al., J. Am. Chem.Soc., 106, 5208 (1984).
G. C. Ness et al, Archives of Biochemistry and Biophysics 197, 493-499 (1979).
F. A. Carey and R. J. Sundberg, Advanced Organic Chemistry, Part A, Second Edition Plenum Press (1984) pp. 73-76.
Chem. Letters, No. 7, (1985), Tokyo, pp. 1007-1008.

*Primary Examiner*—Alan L. Rotman
*Assistant Examiner*—Phyllis G. Spivack
*Attorney, Agent, or Firm*—Kevin T. Mansfield; Marla J. Mathias

[57] ABSTRACT

There is disclosed a process for the asymmetrical hydrogenation of (E)-2-methyl-3-phenyl-2-propen-1-ol of formula

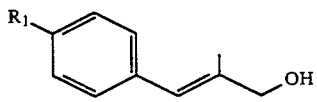

wherein $R_1$ is as defined herein, to give compounds of formula

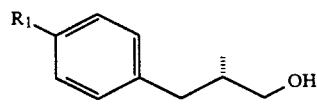

The catalyst is a neutral or cationic rhodium complex of a chiral atropisomeric phosphine.

6 Claims, No Drawings

ASYMMETRICAL HYDROGENATION

This is a divisional of Ser. No. 811,381, filed Dec. 20, 1991, now abandoned.

The present invention relates to an asymmetrical hydrogenation, more specifically to a process for the preparation of compounds of formula

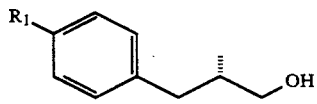   I wherein $R_1$ is hydrogen or a group Z, where

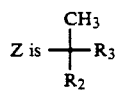

wherein $R_2$ is methyl, ethyl or chloromethyl, and $R_3$ is $C_1$–$C_4$alkyl, or $R_2$ and $R_3$, together with the linking carbon atom, are $C_3$–$C_7$cycloalkyl.

The process of this invention comprises asymmetrically hydrogenating a compound of formula

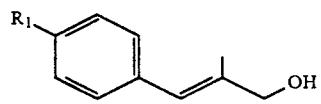   II wherein $R_1$ is as defined above.

The asymmetrical hydrogenation is conveniently carried out using a neutral or cationic rhodium complex of a chiral atropisomeric phosphine. In particular, the hydrogenation can be carried out in the presence of a rhodium catalyst of formula

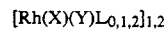   V or

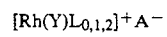   VI wherein
X is a co-ordinating anionic ligand, such as halogen, a carboxylic acid radical, a 1,3-diketonate, for example an acetylacetonate, an (unsubstituted or substituted) phenolate, hydroxy, nitrate, nitrite, cyanate, thiocyanate, cyanide, hydrogensulfate,
Y is a chiral atropisomeric diphosphine ligand, for example a ligand of formula VII or VIII

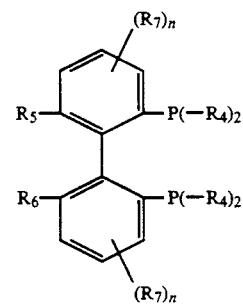   VII wherein $R_4$ is aryl or cyclohexyl, $R_5$ and $R_6$ are the same or different members of the group consisting of lower alkyl, lower alkoxy, di-lower alkylamino and protected hydroxymethyl, or $R_5$ and $R_6$, when taken together, are a group selected from

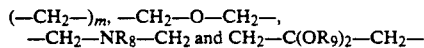

where m is an integer from 3 to 5, $R_8$ is lower alkyl, aryl or benzyl, and $R_9$ is lower alkyl, or both substituents $R_9$ together are di- or trimethylene, $R_7$ is methyl, lower alkoxy, di-lower alkylamino or halogen, and n is 0, 1, 2 or 3;

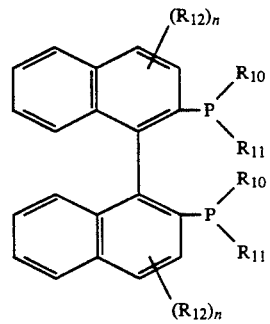   VIII wherein $R_{10}$ and $R_{11}$ are aryl or cyclohexyl, and $R_{12}$ is methyl, ethyl, halogen, —OH, $NH_2$, acetylamino, nitro, —$SO_3H$, preferably in 5,5'position;
L is a neutral ligand, and
$A^-$ is an anion, preferably $BF_4^-$.

The compounds of formulae VII and VIII are used in the (R)-form in the process of this invention.

Within the scope of this invention, halogen may be taken to mean fluoro, chloro, bromo or iodo.

Preferred ligands are those of formula VII, of which in turn those ligands are preferred wherein $R_4$ is unsubstituted or methyl-substituted phenyl, $R_5$ and $R_6$ are identical and are lower alkyl or alkoxy or, when taken together, are the group —$CH_2$—O—$CH_2$—, n is 0 or 1, and $R_7$ is methyl, fluoro or di-lower alkylamino. If n is 1, the substituent $R_7$ is preferably in meta-position to the phosphorus atom.

Illustrative examples of especially preferred ligands of formula VII are:
R-(6,6'-dimethyl-2,2'-biphenylylene)bis(diphenylphosphine);
R-(6,6'-dimethyl-2,2'-biphenylylene)bis(di-p-tolylphosphine);
R-(6,6'-dimethoxy-2,2'-biphenylylene)bis(diphenylphosphine);
R-(6,6'-dimethoxy-2,2'-biphenylylene)bis(di-p-tolylphosphine).

The ligands of formulae VII and VIII are known compounds or they can be prepared in a manner which is known per se.

Within the scope of this invention, the term "lower alkyl" may be taken to mean straight-chain or branched alkyl groups of 1 to 9 carbon atoms, including methyl, ethyl, propyl, isopropyl, n-butyl, isobutyl, tert-butyl, pentyl, hexyl, heptyl, octyl or nonyl. Halogen is fluoro, chloro, bromo or iodo.

The $C_1$–$C_4$alkyl radicals may also be straight-chain or branched.

The term "aryl" in the definition of the compounds of formulae VII and VIII may be taken to mean within the scope of this invention unsubstituted phenyl and phenyl which is substituted in ortho-, para- and/or meta-position by lower alkyl or lower alkoxy groups, preferably methyl or methoxy groups, or also di-lower alkylamino, preferably dimethylamino groups.

The term "lower alkoxy" may be taken to mean groups in which the alkyl moiety is as previously defined. The symbol "⦀⦀⦀" means that the radical in question is below the plane of the molecule.

Within the scope of this invention, the term "neutral ligand" may be taken to mean a readily exchangeable ligand such as an olefin, including ethylene, propylene, cyclooctene, 1,5-hexadiene, norbornadiene, 1,5-cyclooctadiene and the like, a nitrile such as acetonitrile or benzonitrile, or also the solvent employed and the like. This ligand can be replaced in the course of the hydrogenation. If more than one such ligand is present, they may also differ from one another.

Surprisingly, it has now been found that, compared with the known catalysts for such purposes, the rhodium diphosphine complexes of formulae V and VI are appreciably more active and enantioselective. This means in particular that substantially smaller amounts of catalyst can be used, that shorter reaction times are possible, and that optical yields (e.e.) of more than 95% can be obtained.

The asymmetrical hydrogenations can be carried out in suitable organic solvents which are inert under the reaction conditions. Such solvents are typically aromatic hydrocarbons such as benzene or toluene, cyclic ethers such as tetrahydrofuran or dioxane, esters, such as ethyl acetate, or also mixtures thereof, and the like. The ratio of rhodium to ligand Y is conveniently from about 0.05 to about 5 mol, preferably from about 0.5 to about 2 mol, of rhodium per mol of ligand. The ratio of rhodium to the radical X is from about 0.01 to about 20, preferably from about 0.5 to about 10 mol of rhodium per mol of radical X. The molar ratio of rhodium in the complexes of formulae V and VI to the compounds of formula II to be hydrogenated is conveniently from about 0.001 to about 5 mol %, preferably from about 0.002 to about 0.02 mol %.

The asymmetrical hydrogenations using complexes of formulae V or VI may conveniently be carried out in the temperature range from about 20° C. to about 140° C., preferably from about 80° C. to about 120° C. It is preferred to carry out these hydrogenations under pressure, more particularly under a pressure of about 1 to 100 bar, most preferably from 2 to 60 bar.

The compounds of formula I are valuable intermediates.

These compounds are used preferably for preparing the S-isomers of the compounds of formula

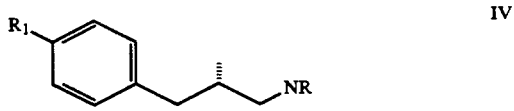

wherein NR is N-piperidyl, 3,5-cis-dimethylpiperidyl, 3-methylpiperidyl or 2,6-dimethyl-4-morpholinyl, into which they can be converted in a manner which is known per se, for example in accordance with the reaction schemes

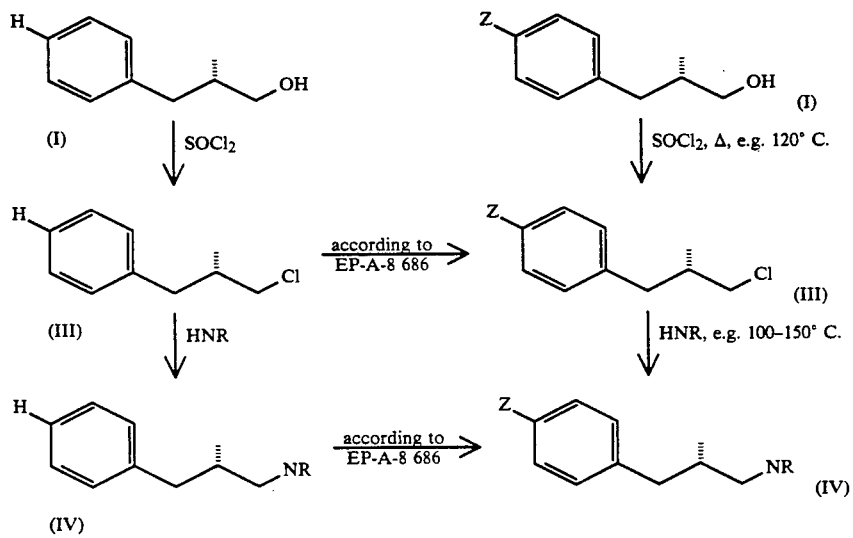

Thus, for example, conventional replacement of the hydroxyl group of I by chlorine, as with $SOCl_2$, gives initially a compound

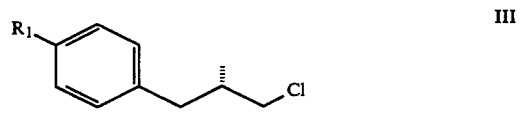

which can be converted into IV by treatment with an amine of formula HNR.

The reaction is conveniently carried out at elevated temperature, and the amine is preferably used in excess, as it acts both as reagent and solvent.

The route described in EP-A-8 686 is also possible, i.e. alkylation of the phenyl radical.

The hydroxyl group of I must itself initially be activated such that a nucleophilic substitution by an amine is possible. The customary groups are accordingly halides (Cl, Br, I), but sulfonates (e.g. tosylate, mesylate) are also useful.

EXAMPLES

| Abbreviations | |
|---|---|
| (R)-BIPHEMP | (R)-(6,6'-dimethyl-2,2'-biphenylylene-bis-(diphenylphosphine)) |

| Abbreviations | |
|---|---|
| (R)-pTolBINAP | [((R)-1,1'-binaphthyl)-2,2'-ylene]bis-(di-p-tolylphosphine) |
| (R)-pTolMeOBIPHEP | [(R)-6,6'-dimethoxy-2,2'-biphenylylene]-bis(di-p-tolylphosphine) |
| (R)-BIPHOMP | [(R)-5,7-dihydro-dibenz[c,e]oxepine-1,11-diyl]bis(diphenylphosphine) |
| AcOEt | ethyl acetate |
| THF | tetrahydrofuran |
| EtOH | ethanol |

Determination of the E.E. Values

To determine the e.e. values the products are converted in methylene chloride with (R)- or (S)-6-methoxy-2,5,7,8-tetramethylchromane-2-carboxylic acid into the diastereomeric isomers and analysed by gas chromatography.

EXAMPLE 1

In a glove box ($O_2$ content < 1 ppm), 39.2 mg (0.049 mmol) of tetrabutylammonium hydroxide 30 hydrate, 7.5 mg (0.049 mmol) of 2,6-dihydroxybenzoic acid, 19.9 mg (0.049 mmol) of bis(1,5-cyclooctadiene)rhodium(I) tetrafluoroborate and 33.2 mg (0.049 mmol) of (R)-ptolBINAP are suspended in 50 mol of toluene in a 50 ml graduated flask. The suspension is then stirred for 1.5 hours at 22° C., whereupon a clear, orange-red catalyst solution forms.

EXAMPLE 2

In a glove box ($O_2$ content < 1 ppm), a 500 ml autoclave is charged with 5.0 g (24.5 mmol) of (E)-dehydroliliol, 145 ml of toluene and 5 ml of the catalyst solution prepared according to Example 1. The hydrogenation is carried out at 100° C. under a constant hydrogen pressure of 60 bar and with efficient stirring. The conversion is >99% after 6 hours. The pale yellow hydrogenation solution is flushed from the autoclave and concentrated by evaporation at 60° C./17 mbar. The residue is distilled at 140° C./0.01 mbar, giving 5.0 g (99.0%) of (S)-liliol as a colourless oil in an enantiomeric purity of 92.4% e.e. $[\alpha]_{365}^{20} = -46.0°$ C. (EtOH, c = 1%).

EXAMPLE 2a

In accordance with the general procedure described in Example 1, a catalyst solution is prepared and the hydrogenation of (E)-dehydroliliol is carried out as described in Example 2. The results are summarised in Table 1.

TABLE 1

| | | | Examples 2a–2i | | | | | | |
|---|---|---|---|---|---|---|---|---|---|
| No 2 | [Rh(X)(Y)(COD)] X | Y | S/C | Solvent | c % | p bar | T °C. | Reaction after 22 h (%) | Liliol e.e. % |
| a | $CH_3OCH_2COO$ | (R)-p-TolBINAP | 5000 | toluene | 3.7 | 60 | 100 | 99.2 | 93.7 (S) |
| b | $Cl_2CHCOO$ | (R)-p-TolBINAP | 5000 | toluene | 3.7 | 60 | 100 | 99.4 | 95.3 (S) |
| c | $C_6H_5COO$ | (R)-p-TolBINAP | 5000 | toluene | 3.7 | 60 | 100 | 100.0 | 94.6 (S) |
| d | $C_6Cl_5OCH_2COO$ | (R)-p-TolBINAP | 5000 | toluene | 3.7 | 60 | 100 | 89.7 | 94.9 (S) |
| e | $(CH_3)_3CCOO$ | (R)-p-TolBINAP | 5000 | toluene | 3.7 | 60 | 100 | 99.7 | 88.1 (S) |
| f | $C_6H_5O$ | (R)-p-TolBINAP | 5000 | toluene | 3.7 | 60 | 100 | 100.0 | 92.8 (S) |
| g | $C_6F_5O$ | (R)-p-TolBINAP | 5000 | toluene | 3.7 | 60 | 100 | 64.2 | 91.7 (S) |
| h | $CH_3COCH_2COCH_3$ | (R)-p-TolBINAP | 5000 | toluene | 3.7 | 60 | 100 | 98.9 | 91.8 (S) |
| i | $CF_3COCH_2COCF_3$ | (R)-p-TolBINAP | 5000 | toluene | 3.7 | 60 | 100 | 96.2 | 93.7 (S) |

EXAMPLE 3

In a glove box ($O_2$ content < 1 ppm), a catalyst solution is prepared by dissolving 15.9 mg (0.024 mmol) of di-μ-trifluoroacetate-bis(1,5-cyclooctadiene)dirhodium and 33.2 mg (0.049 mmol) of (R)-p-TolBINAP in 50 ml of toluene in a 50 ml graduated flask. Then 5 ml of this catalyst solution are added to a solution of 5.0 g (24.47 mmol) of (E)-dehydroliliol in 145 ml of toluene in a 500 ml autoclave. The hydrogenation is carried out at 100° C. under a constant pressure of 60 bar and with efficient stirring. The conversion is 100% after 21 hours. The pale yellow hydrogenation solution is worked up as described in Example 2, giving (S)-liliol in an enantiomeric purity of 91.0% e.e.

EXAMPLE 4

In a glove box ($O_2$ content < 1 ppm), a catalyst solution is prepared by dissolving 19.9 mg (0.0493 mmol) of bis(1,5-cyclooctadiene)rhodium(I) tetrafluoroborate, 33.2 mg (0.0493 mmol) of (R)-p-TolBINAP and 14.9 mg (0.0493 mmol) of tetrabutylammonium nitrate in 100 ml of toluene in a 100 ml graduated flask. Then 10 ml of this catalyst solution are added to a solution of 5.0 g (24.47 mmol) of (E)-dehydroliliol in 140 ml of toluene in a 500 ml autoclave. The hydrogenation is carried out at 100° C. under a constant pressure of 60 bar and with efficient stirring. The conversion is 99.8% after 17 hours. The pale yellow hydrogenation solution is worked up as described in Example 2, giving (S)-liliol in an enantiomeric purity of 94.6% e.e.

$[\alpha]_{365}^{20} = -47.6°$ C. (EtOH, c = 1%).

EXAMPLE 4a

In accordance with the general procedure described in Example 4, a catalyst solution is prepared and the hydrogenation of (E)-dehydroliliol is carried out. The results are summarised in Table 2.

TABLE 2

| | | | Examples 4a–4l | | | | | | |
|---|---|---|---|---|---|---|---|---|---|
| No 4 | [Rh(X)(Y)(COD)] X | Y | S/C | Solvent | c % | p bar | T °C. | Reaction after 22 h (%) | Liliol e.e. % |
| a | $CH_3COO$ | (R)-p-TolBINAP | 10000 | toluene | 11.0 | 60 | 100 | 36.2 | 92.6 (S) |
| b | F | (R)-p-TolBINAP | 10000 | toluene | 11.0 | 60 | 100 | 53 | 92.3 (S) |
| c | Br | (R)-p-TolBINAP | 10000 | toluene | 11.0 | 60 | 100 | 96.8 | 96.2 (S) |
| d | I | (R)-p-TolBINAP | 10000 | toluene | 11.0 | 60 | 100 | 87.9 | 95.8 (S) |
| e | $NO_3$ | (R)-p-TolBINAP | 5000 | toluene | 3.7 | 60 | 100 | 99.8 | 94.6 (S) |
| f | $NO_2$ | (R)-p-TolBINAP | 5000 | toluene | 3.7 | 60 | 100 | 98.7 | 91.7 (S) |

TABLE 2-continued

| | | Examples 4a–4l | | | | | | |
|---|---|---|---|---|---|---|---|---|
| No 4 | [Rh(X)(Y)(COD)] X | Y | S/C | Solvent | c % | p bar | T °C. | Reaction after 22 h (%) | Liliol e.e. % |
| g | OH | (R)-p-TolBINAP | 5000 | toluene | 3.7 | 60 | 100 | 99.3 | 89.7 (S) |
| h | CN | (R)-p-TolBINAP | 5000 | toluene | 3.7 | 60 | 100 | 97.9 | 95.5 (S) |
| i | SCN | (R)-p-TolBINAP | 5000 | toluene | 3.7 | 60 | 100 | 94.6 | 95.4 (S) |
| j | OCN | (R)-p-TolBINAP | 5000 | toluene | 3.7 | 60 | 100 | 98.5 | 93.7 (S) |
| k | HSO$_4$ | (R)-p-TolBINAP | 5000 | toluene | 3.7 | 60 | 100 | 48.8 | 88.0 (S) |
| l | H$_2$PO$_4$ | (R)-p-TolBINAP | 5000 | toluene | 3.7 | 60 | 100 | 99.0 | 88.2 (S) |

EXAMPLE 5

In a glove box (O$_2$ content <1 ppm), a catalyst solution is prepared by dissolving 24.3 mg (0.0493 mmol) of dichloro-bis(1,5-cyclooctadiene)dirhodium and 66.9 mg (0.0986 mmol) of (R)-p-TolBINAP in 50 ml of toluene in a 50 ml graduated flask. Then 2 ml of this catalyst solution are added to a solution of 16.1 g (78.85 mmol) of (E)-dehydroliliol in 148 ml of toluene in a 500 ml autoclave. The hydrogenation is carried out at 100° C. under a constant pressure of 60 bar and with efficient stirring. The conversion is 99.6% after 21 hours. The pale yellow hydrogenation solution is worked up as described in Example 2, giving (S)-liliol in an enantiomeric purity of 95.1% e.e. $[\alpha]_{365}^{20} = -47.0°$ C. (EtOH, c=1%).

EXAMPLE 5a

The catalyst solution is prepared in accordance with the general procedure described in Example 5, and the hydrogenation is carried out under the conditions shown in Table 3. The hydrogenation solution is worked up as described in Example 2. The results are summarised in Table 3.

EXAMPLE 7

In a glove box (O$_2$ content <1 ppm), a catalyst solution is prepared by dissolving 9.15 mg (0.0186 mmol) of dichloro-bis(1,5-cyclooctadiene)dirhodium and 25.18 mg (0.0371 mmol) of (R)-p-TolBINAP in 50 ml of toluene. This catalyst solution is then added to a solution of 5.5 g (37.1 mmol) of (E)-2-methyl-3-phenyl-2-propen-1-ol in 35 ml of toluene in a 500 ml autoclave. The hydrogenation is carried out at 100° C. under a constant pressure of 60 bar and with efficient stirring. The conversion is 100% after 22 hours. The pale yellow hydrogenation solution is worked up as described in Example 2, giving (S)-2-methyl-3-phenylpropan-1-ol in an enantiomeric purity of 89.1% e.e.

$[\alpha]_{365}^{20} = -57.9°$ C. (EtOH, c=1%).

EXAMPLE 8

(a)

(S)-1-tert-Butyl-4-[3-chloro-2-methylpropyl]benzene 30.9 g (0.15 mol) of (S)-3-(p-tert-butylphenyl)-2-methyl-1-propanol (S-liliol) are charged to the reactor and, with stirring, 20.2 g (0.17 mol) of thionyl chloride are added at 120° C. over 5 hours. The gaseous products

TABLE 3

| | | Examples 5a–5j | | | | | | |
|---|---|---|---|---|---|---|---|---|
| No 5 | [Rh(X)(Y)(COD)] X | Y | S/C | Solvent | c % | p bar | T °C. | Reaction after 22 h (%) | Liliol e.e. % |
| a | Cl | (R)-BIPHEMP | 200 | toluene | 11 | 60 | 20 | 100.0 | 93.0 (S) |
| b | Cl | (R)-BIPHEMP | 200 | toluene | 11 | 60 | 60 | 100.0 | 93.7 (S) |
| c | Cl | (R)-p-TolBINAP | 20000 | toluene | 11 | 60 | 120 | 99.0 | 91.0 (S) |
| d | Cl | (R)-p-TolBINAP | 20000 | toluene | 11 | 30 | 100 | 90.5 | 96.4 (S) |
| e | Cl | (R)-p-TolBINAP | 20000 | toluene | 11 | 5 | 100 | 25.6 | 94.6 (S) |
| f | Cl | (R)-p-TolBINAP | 20000 | toluene | 30 | 60 | 100 | 53.0 | 90.9 (S) |
| g | Cl | (R)-p-TolMe-OBIPHEP | 20000 | toluene | 11 | 60 | 100 | 100 | 94.2 (S) |
| h | Cl | (R)-BIPHOMP | 20000 | toluene | 11 | 60 | 100 | 100 | 92.6 (S) |
| i | Cl | (R)-BIPHEMP | 200 | THF | 11 | 60 | 60 | 100 | 93.7 (S) |
| j | Cl | (R)-p-TolBINAP | 10000 | AcOEt | 11 | 60 | 100 | 99 | 95.2 (S) |

EXAMPLE 6

In a glove box (O$_2$ content <1 ppm), a catalyst solution is prepared by dissolving 32.0 mg (0.079 mmol) of bis(1,5-cyclooctadiene)rhodium(I) tetrafluoroborate and 53.5 mg (0.079 mmol) of (R)-p-TolBINAP in 50 ml toluene in a 50 ml graduated flask. Then 5 ml of this catalyst solution are added to a solution of 16.1 g (78.85 mmol) of (E)-dehydroliliol in 145 ml of toluene in a 500 ml autoclave. The hydrogenation is carried out at 100° C. under a constant pressure of 60 bar and with efficient stirring. The conversion is 99.8% after 22 hours. The pale yellow hydrogenation solution is worked up as described in Example 2, giving (S)-liliol in an enantiomeric purity of 95.4% e.e. $[\alpha]_{365}^{20} = -47.5°$ C. (EtOH, c=1%).

which form (SO$_2$, HCl) are destroyed by passing them into a wash tower filled with 10% sodium hydroxide solution. When the dropwise addition is complete, the reaction mixture is stirred for ½ hour at 120° C. and then cooled. The crude product is distilled under a high vacuum (b.p. about 80° C.), giving (a) as a colourless oil.

(b) (S)-2-Methyl-3-phenylpropyl chloride

In accordance with the general procedure described in Example 8 (a), 22.5 g (0.15 mol) of (S)-2-methyl-3-phenylpropanol are reacted with 20.2 g (0.17 mol) of thionyl chloride, and the crude product is distilled under a high vacuum (18 torr) to give (b) (b.p. 110°–112° C.) as a colourless oil.

Product (b) can then be converted in known manner into product (a) by a Friedel-Craft alkylation, as with isobutylene in conc. sulfuric acid.

The reaction of (a) with piperidine gives the novel compound (S)-fenpropidine.

The reaction of (a) with cis-2,6-dimethylmorpholine gives the known (S)-fenpropimorph.

(S)-1-[3-p-tert-Butylphenyl)-2-methylpropyl]piperidine ((S)fenpropidine)

With efficient stirring, 27 g (0.12 mol) of (S)-1-tert-butyl-4-[3-chloro-2-methylpropyl]benzene in 70 ml (0.708 mol) of piperidine are heated for 16 hours to reflux temperature. Then a further 30 ml (0.303 mol) of piperidine are added. The reaction course is monitored by gas chromatography. The reaction mixture is stirred for a further hour at reflux temperature and allowed to cool. The reaction mixture is poured into 350 ml of sodium hydroxide solution and extracted with altogether 600 ml of n-hexane in 3 portions. The organic phases are combined, dried over anhydrous sodium sulfate and concentrated. The residue is chromatographed on 700 g of silica gel 60 (MERCK, granular size 0.040–0.063) with a 1:1 mixture of ethyl acetate/n-hexane. The pure fractions are combined and distilled under a high vacuum (b.p. about 140° C.), giving a colourless oil. Optical rotation (c=1%, $C_2H_5OH$ 96%):

365 nm+11.1°
436 nm+9.0°
546 nm+6.0°
578 nm+5.5°
589 nm+5.4°

The enantiomeric purity can be determined in the NMR spectrum ($CDCl_3$) by addition of the "chiral solvent" (R)-(−)-2,2,2-trifluoro-1-(9-anthryl) ethanol. The shifts in the signals of the methyl group at the centre of chirality depends on the relative amount of TAE in the solution. No indication of racemisation is found.

The reaction of Example 8(a) with cis-3,5-dimethylpiperidine leads to the novel compound cis-1-[(S)-3-(p-tert-butylphenyl)-2-methylpropyl]-3,5-dimethylpiperidine in the form of a colourless oil. Optical rotation in 1% ethanol: $[\alpha]_{546} = +6.1°$.

The reaction of (a) with racemic 3-methylpiperidine leads to the novel fungicide (RS)-1-[(S)-3-p-tert-butylphenyl)-2-methylpropyl]-3-methylpiperidine (epimer ratio 1:1) in the form of a colourless oil.

EXAMPLE 9

Starting from (S)-2-methyl-3-phenylpropan-1-ol prepared according to Example 7, the following novel fungicidally active compounds are prepared in accordance with the above reaction scheme:

(S)-1-[3-(p-tert-amylphenyl)-2-methylpropyl]piperidine as a colourless oil; optical rotation in 0.5% ethanol: $[\alpha]_{546} = +5.8°$.

cis-1-[(S)-3-(p-tert-amylphenyl)-2-methylpropyl]3,5-dimethylpiperidine as a colourless oil; optical rotation in 1% ethanol; $[\alpha]_{546} = +8.2°$.

(RS)-1[(S)-3-(p-tert-amylphenyl)-2-methylpropyl]-3-methylpiperidine as a colourless oil. Mass spectrum: $M^{(+)}$ 301 (2%), 112 (100%).

What is claimed is:

1. A process for the preparation of a compound of the formula

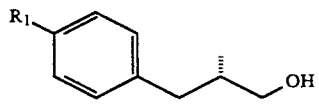

wherein the compound of formula I is produced in an optical purity of 90% or more, wherein
$R_1$ is hydrogen or a group Z, where
Z is

$R_2$ methyl, ethyl or chloromethyl;
$R_3$ is $C_1$–$C_4$alkyl, or $R_2$ and $R_3$, together with the linking carbon atom, are $C_3$–$C_7$cycloalkyl;
which process comprises asymmetrically hydrogenating a compound of the formula

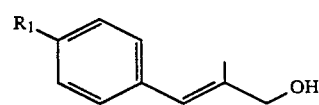

in the E-form, wherein $R_1$ is defined as above, in the presence of a rhodium catalyst of the formula V or VI

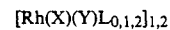     V or

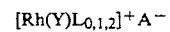     VI wherein
X is a halide, a carboxylic acid anion, an 1,3-diketonate anion, a phenolate anion, or which is hydroxy, nitrate, nitrite, cyanate, thiocyanate, cyanide or hydrogensulfate;
Y is a chiral atropisomeric diphosphine ligand of the formula VII or VIII

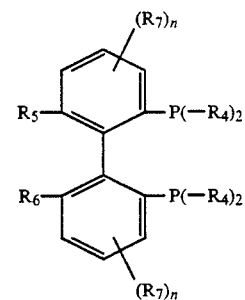

wherein
$R_4$ is cyclohexyl or phenyl which is unsubstituted or substituted by lower alkyl or lower alkoxy groups or by di-lower alkylamino groups;
$R_5$ and $R_6$ are the same or different members of the group consisting of lower alkyl, lower alkoxy, di-lower alkylamino and protected hydroxymethyl, or $R_5$ and $R_6$, when taken together, is a group selected from (—CH$_2$—)$_m$, —CH$_2$—O—CH$_2$—, —CH$_2$—NR- 8—CH$_2$ and CH$_2$—C(OR$_9$)$_2$—CH$_2$— where m is an integer from 3 to 5;

R$_8$ is lower alkyl, benzyl or phenyl which is unsubstituted or substituted by lower alkyl or lower alkoxy groups or by di-lower alkylamino groups;

R$_9$ is lower alkyl, or both substituents R$_9$ together are di- or trimethylene;

R$_7$ is methyl, lower alkoxy, di-lower alkylamino or halogen, and n is 0, 1, 2 or 3;

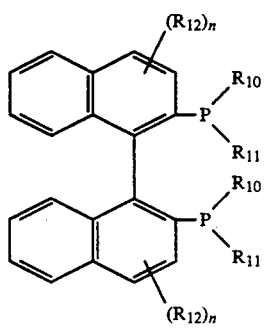

VIII wherein

R$_{10}$ and R$_{11}$ are cyclohexyl or phenyl which is unsubstituted or substituted by lower alkyl or lower alkoxy groups or by di-lower alkylamino groups;

R$_{12}$ is methyl, ethyl, halogen, OH, NH$_2$, acetylamino, nitro or SO$_3$H;

L is an olefin selected from the group consisting of ethylene, propylene, cyclooctene, 1,5-hexadiene, norbornadiene and 1,5-cyclooctadiene, a nitrile selected from the group consisting of acetonitrile and benzonitrile, or a solvent molecule, and A$^-$ is an anion.

2. A process according to claim 1, wherein the temperature is from 20° C. to 140° C.

3. A process according to claim 2, wherein the temperature is from 80° C. to 120° C.

4. A process according to claim 1, wherein in formula VIII, R$_{12}$ is in the 5,5'-position, A$^-$ is BF$_4^-$ and n is 1.

5. A process according to claim 1, wherein the molar ratio of rhodium in the complexes of the formulae V or VI to the compound of formula II to be hydrogenated is from 0.001 to 5 mol %.

6. A process according to claim 5, wherein the molar ratio is from 0.002 to 0.02 mol %.

* * * * *